US00PP19372P2

(12) United States Plant Patent
Kaagman

(10) Patent No.: US PP19,372 P2
(45) Date of Patent: Oct. 21, 2008

(54) *DAHLIA* PLANT NAMED 'GOALIA SCARL'

(50) Latin Name: *Dahlia variabilis*
Varietal Denomination: Goalia Scarl

(75) Inventor: Pim Kaagman, Andijk (NL)

(73) Assignee: Goldsmith Seeds Europe B.V., Andijk (NL)

( * ) Notice: Subject to any disclaimer, the term of this patent is extended or adjusted under 35 U.S.C. 154(b) by 0 days.

(21) Appl. No.: 11/894,582

(22) Filed: Aug. 21, 2007

(51) Int. Cl.
*A01H 5/00* (2006.01)

(52) U.S. Cl. ..... Plt./321

(58) Field of Classification Search ..... Plt./321
See application file for complete search history.

(56) References Cited

PUBLICATIONS

UPOV ROM GTITM Computerdatabase, GTI Jouve Retrieval Software, May 2007, Citations for 'Goalia Scarl'.*

* cited by examiner

*Primary Examiner*—Wendy C. Haas
(74) *Attorney, Agent, or Firm*—Jondle & Associates, P.C.

(57) ABSTRACT

A new *Dhalia* plant particularly distinguished by its large scarlet flowers, a full plant habit, and small, dark green leaves foliage is disclosed.

2 Drawing Sheets

Genus and species: *Dahlia variabilis.*
Variety denomination: 'Goalia Scarl'.

BACKGROUND OF THE NEW PLANT

The present invention comprises a new and distinct cultivar of *Dahlia,* botanically known as *Dahlia variabilis,* and hereinafter referred to by the cultivar name 'Goalia Scarl'. The new cultivar originated from a hybridization made in June 1999 in Andijk, The Netherlands. The female parent was the bronze-yellow-flowered *Dahlia* proprietary line 'DT-32-2' (unpatented), and the male parent was the orange-flowered *Dhalia* proprietary line 'DU-43-1' (unpatented). The seeds produced by the hybridization were sown in February 2002 in Andijk, The Netherlands. A single plant selection was chosen for further evaluation and for asexual propagation in May 2002 in Andijk, The Netherlands.

The new cultivar was created in 1999 in Andijk, The Netherlands and has been asexually reproduced repeatedly by vegetative cuttings and tissue culture in Andijk, The Netherlands, and Gilroy, Calif. over a five-year period. The plant has also been trialed at Gilroy, Calif., Michigan, Andijk, The Netherlands and Hillscheid, Germany. The present invention has found to retain its distinctive characteristics through successive asexual propagations.

Plant Breeder's Rights for this cultivar were applied for in the European Union on Jun. 19, 2006 and Canada on Oct. 3, 2006. 'Goalia Scarl' has not been made publicly available more than one year prior to filing of this application.

SUMMARY OF THE INVENTION

The following are the most outstanding and distinguishing characteristics of this new cultivar when grown under normal horticultural practices in Gilroy, Calif.

1. Large, scarlet flowers;
2. A full plant habit; and
3. Small, dark green leaves.

DESCRIPTION OF THE PHOTOGRAPHS

This new *Dahlia* plant is illustrated by the accompanying photographs which show overall plant habit including blooms, buds, and foliage of the plant; the photographs are of 20-to 24-week old plants grown in a greenhouse in Hillschied, Germany in 2006; the colors shown are as true as can be reasonably obtained by conventional photographic procedures.

DESCRIPTION OF THE NEW CULTIVAR

Figure 1:
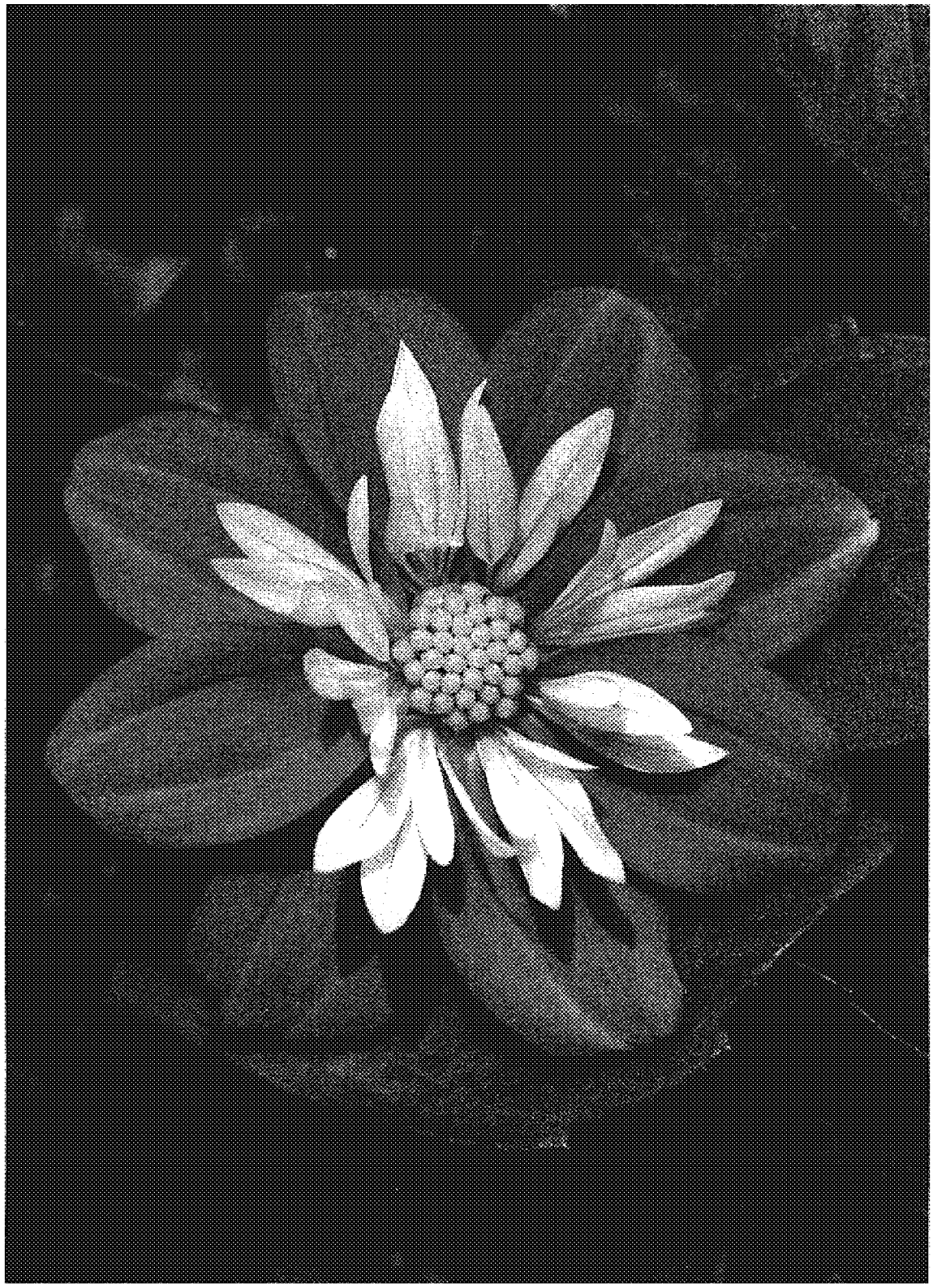
FIG. 1 shows a close-up of the mature flowers.
Figure 2:
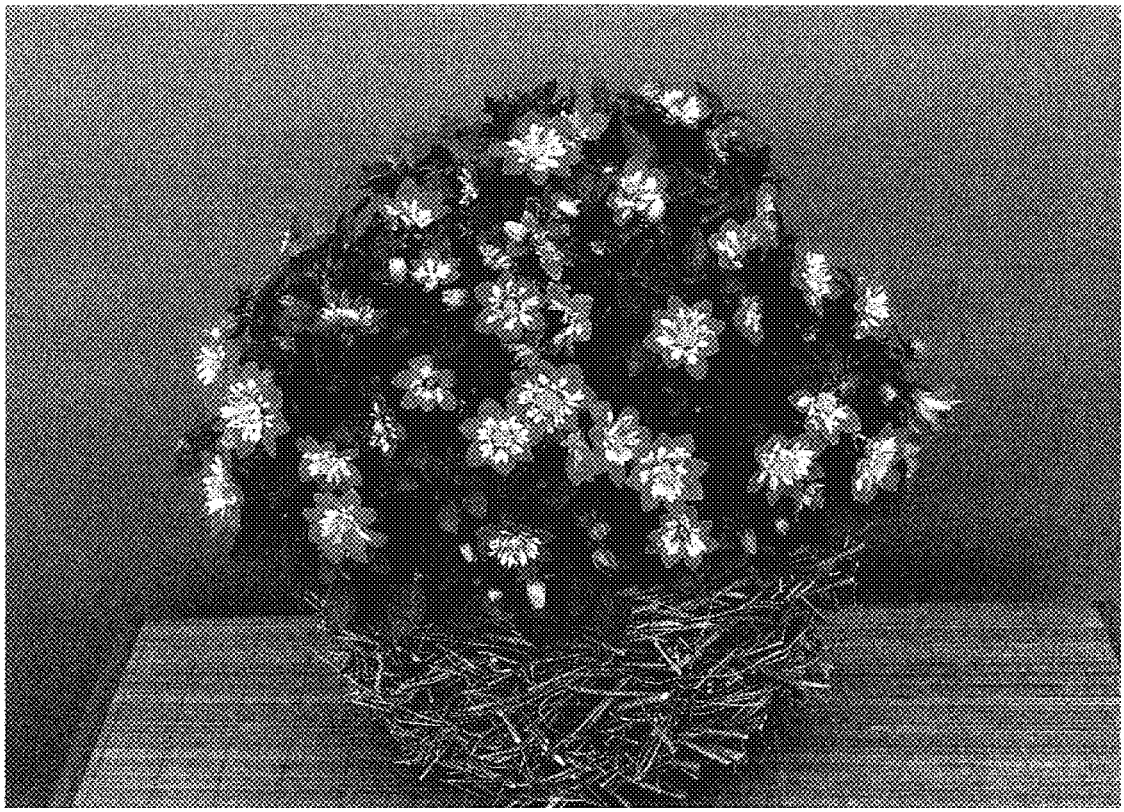
FIG. 2 shows the overall plant habit, including blooms, buds, and foliage.

The following detailed descriptions set forth the distinctive characteristics of 'Goalia Scarl'. The data which define these characteristics were collected from asexual reproductions carried out in Ontario, Canada. The plant history was taken on 16-week-old plants grown in 6-inch azalea pots in the spring and summer seasons in a greenhouse. Two terminal pinches were made at a young plant stage. No plant growth regulators were used. The plants were grown under a poly covered hoop and then moved indoor. Color readings were taken outdoors in the summer season under natural light. Color references are primarily to the R.H.S. Colour Chart of The Royal Horticultural Society of London (R.H.S.) (2001 edition).

DESCRIPTION OF THE NEW PLANT

Classification:
*Family.*—Asteraceae.
*Botanical name.*—*Dahlia variabilis.*

Parentage:
*Female parent.*—'DT-32-2' bronze-yellow-followered *Dahlia* proprietary line (unpatented).
*Male parent.*—'DU-43-1' orange-flowered *Dhalia* proprietary line (unpatented).

Growth:

*Form.*—Upright.

*Habit.*—Compact and mounding.

*Growth and branching habit.*—Good, vigorous habit; excellent branching.

*Height* (*from top of soil*).—14.0 cm to 17.0 cm.

*Width.*—26.0 cm to 30.0 cm.

*Time to produce a finished flowering plant.*—7 to 9 weeks for a 4-to 6-inch pot.

*Outdoor plant performance.*—Free flowering, used in patio planters, mixed-container plantings, or in garden beds.

*Time to initiate and develop roots.*—22 to 28 days.

*Root description.*—Fibrous and white.

Leaves:

*Arrangement.*—Opposite, single, simple.

*Shape.*—Ovate to elliptical; many are somewhat puckered looking.

*Apex.*—Acute.

*Base.*—Attenuate.

*Margin.*—Slightly serrate.

*Length* (*fully expanded*).—4.1 cm to 4.3 cm.

*Width* (*fully expanded*).—2.0 cm to 2.1 cm.

*Texture.*—Leathery, smooth.

*Color.*—Immature: Upper surface: RHS 137B. Lower surface: RHS 148D with a silvery sheen. Mature: Upper surface: RHS 137A. Lower surface: RHS 148D with a silvery sheen.

*Venation.*—Arrangement: Pinnate. Color: RHS 143C.

*Petiole.*—Color: RHS 143C along the edges and almost transparent in the middle. Length: 1.0 cm to 1.2 cm. Width: 0.25 cm. Texture: Smooth, glabrous.

Stems:

*Number of branches per plant.*—4 to 6.

*Length.*—14.0 cm to 16.2 cm.

*Diameter.*—0.45 cm.

*Internode length.*—2.2 cm to 2.5 cm.

*Color.*—RHS 146B, with some RHS 143C blotches mixed in.

*Texture.*—Smooth, glabrous.

*Anthocyanin.*—Absent.

*Penduncle.*—Color: Closest to RHS 143C. Length: 6.1 cm to 6.4 cm. Diameter: 0.25 cm to 0.3 cm. Texture: Smooth, glabrous.

Bud:

*Shape.*—Orbicular where immature, to ovate when mature.

*Diameter.*—0.8 cm to 1.0 cm.

*Length.*—0.7 cm to 0.9 cm.

*Color* (*just before ray florets unfold*).—RHS 45B.

Inflorescence

*Type.*—Composite; borne on terminals above foliage; semi-double flowers, florets face upward or outward.

*Blooming habit.*—Continuous throughout the growing season; excellent floriferousness.

*Quantity of inflorescences per plant.*—15 to 20.

*Lastingness of individual blooms on the plant.*—7 to 12 days.

*Fragrance.*—None.

*Inflorescence diameter.*—6.5 cm to 7.5 cm.

*Disc diameter.*—1.2 cm to 1.4 cm.

Disc floret:

*Quantity (per inflorescence).*—30 to 40.

*Shape.*—Elongated, cylindrical, shiny.

*Color.*—RHS 15B.

*Length.*—1.0 cm to 1.1 cm.

*Diameter.*—0.2 cm to 0.3 cm.

*Apex.*—5-pointed, each acute.

*Ray floret.*—Quantity: 8. Length: 2.5 cm to 2.9 cm. Width: 1.6 cm to 1.9 cm. Color: Upper surface: RHS 46B with some darker hues of RHS 46A; fading to between RHS 44A, RHS 44B and RHS 44C Lower surface: Closest to RHS 45B or RHS 44C with stripes of RHS 3C. Apex: Praemorse. Base: Fused. Margin: Entire. Texture: Papillose.

*Petaloids.*—Quantity: 4 to 5 per ray floret. Color (both surfaces): RHS 1B; many with a slight hue of RHS 144A at the side margins. Length: 1.9 cm to 2.1 cm. Diameter: 0.5 cm. Shape: Narrow elliptic. Apex: Acute. Margin: Entire. Base: Fused. Texture: Papillose.

*Involucral bracts.*—Quantity (per inflorescence): 5. Shape: Elliptical. Length: 1.2 cm to 1.3 cm. Width: 0.4 cm to 0.5 cm. Color: RHS 137B. Apex: Acute. Base: Attenuate. Margin: Entire. Texture: Smooth, glabrous.

Reproductive organs:

*Androecium.*—Location: Present on disc florets only. Quantity per floret: 1. Anther: Color: RHS 14A. Length: 0.4 cm. Filament length: 0.8 cm. Filament color: RHS N155C. Pollen color: RHS 17B. Pollen amount: Moderate.

*Gynoecium.*—Location: Present on ray and disc florets. Quantity per floret: 1. Pistil length: Ray florets: 0.1 cm to 0.3 cm. Disc florets: 1.4 cm. Stigma: Color: RHS 13B. Style: Color: RHS 154B.

Fruit and seed set: Has not been observed.

Disease and insect resistance: Has not been observed.

COMPARISON WITH PARENTAL AND COMMERCIAL CULTIVARS

'Goalia Scarl' differs from the female parent, 'DT-32-2' (unpatented) in that 'Goalia Scarl' has a larger flower with a scarlet color and a fuller plant habit than 'DT-32-2'.

'Goalia Scarl' differs from the male parent, 'DU-43-1' (unpatented) in that 'Goalia Scarl' has scarlet-colored flowers, and smaller darker leaves than 'DU-43-1'.

'Goalia Scarl' differs from the commercial cultivar 'Hawaii' (unpatented) (European Union Plant Variety Propection Application No. EU11446) in that 'Goalia Scarl' has a more scarlet-red, collerette type flower that fades more than 'Hawaii'. Additionally, 'Goalia Scarl' has smaller leaves with weaker serrations than 'Hawaii'.

I claim:

1. A new and distinct cultivar of *Dahlia* plant as shown and described herein.

* * * * *